United States Patent
Naik et al.

(10) Patent No.: US 6,613,947 B1
(45) Date of Patent: Sep. 2, 2003

(54) HIGH PURITY 4,4'-ISOPROPYLIDENE-BIS-(2,6 DIBROMOPHENOL) AND PROCESS FOR THE PREPARATION OF SUCH HIGH PURITY 4,4'-ISOPROPYLIDENE-BIS-(2,6 DIBROMOPHENOL)

(75) Inventors: Shantaram Narayan Naik, Karnataka (IN); Dharma Ratnakar Ramdas Naik, Karnataka (IN); M. Madhusudan Rao, Kutchellapadu (IN)

(73) Assignee: Solaris Chemtech Limited (IN)

( * ) Notice: Subject to any disclaimer, the term of this patent is extended or adjusted under 35 U.S.C. 154(b) by 0 days.

(21) Appl. No.: 10/168,454

(22) PCT Filed: Dec. 20, 1999

(86) PCT No.: PCT/IN99/00073

§ 371 (c)(1),
(2), (4) Date: Oct. 21, 2002

(87) PCT Pub. No.: WO01/46106

PCT Pub. Date: Jun. 28, 2001

(51) Int. Cl.$^7$ ................................. C07C 39/16
(52) U.S. Cl. .................................. 568/726; 568/725
(58) Field of Search ................. 568/725, 726

(56) References Cited

U.S. PATENT DOCUMENTS 5,059,726 A * 10/1991 Eguchi
5,068,463 A * 11/1991 Walter
5,107,035 A *  4/1992 Hines
5,138,103 A *  8/1992 Eguchi
5,208,389 A *  5/1993 McKinnie
5,237,112 A *  8/1993 LaRose
5,302,761 A *  4/1994 Tamabayashi
6,245,950 B1 *  6/2001 Kantam

* cited by examiner

Primary Examiner—Michael L. Shippen
(74) Attorney, Agent, or Firm—Pendorf & Cutliff

(57) ABSTRACT

A high purity 4,4'-isopropylidine-bis-(2,6-dibromophenol) characterised by ionic bromides less than 10 ppm, colour in alkaline solution from 60–100 HU, HPLC purity about 99.9%, APHA of 20% MeOH solution less than 10.0 HU, Fe less than 1.0 ppm, turbidity of 20% MeOH solution less than 5 NTU, pH of 10% slurry 6.0–7.0, size of the crystal particles, 250 to 280 microns with angle of repose lower than 30. The product is produced by reacting Bisphenol-A with bromine in a "water-immiscible" polar solvent in the presence of hydrogen peroxide, aging the reaction products after the reaction, eliminating the excess bromine by reducing agents, washing the product layer with a combination of anionic surfactant, alkali, reducing agent and demineralised water under controlled pH conditions, partially distilling the organic solvent chilling the medium containing the product, filtering the crude product, boiling the crude product with alkali, reducing agent and demineralised water, filtering the TBBA, washing the product with demineralised water and drying to obtain the final high purity TBBA with high yield.

11 Claims, No Drawings

HIGH PURITY 4,4'-ISOPROPYLIDENE-BIS-(2,6 DIBROMOPHENOL) AND PROCESS FOR THE PREPARATION OF SUCH HIGH PURITY 4,4'-ISOPROPYLIDENE-BIS-(2,6 DIBROMOPHENOL)

FIELD OF THE INVENTION

The present invention relates to a high purity 4,4'-isopropylidine-bis-(2.6 dibromophenol) also called Tetrabromobisphenol A (TBBA) and also to a process for the preparation of such high purity Tetrabromobisphenol A (TBBA).

BACKGROUND

Tetrabromobisphenol A (TBBA) which has the chemical name of 4–4'-isopropylidine-bis-(2,6-dibromophenol) [abbreviated as TBBA] is a specialty chemical with wide range of applications in industry especially as a

- Reactive flame retardant to produce epoxy resins used for electronic encapsulation compounds printed circuit boards, housing components for household goods and electronic goods.
- Additive flame retardant in ABS where it is used as a substitute for octabromo dipheryl oxide.
- Additive for polycarbonates and unsaturated polyester resins.
- Raw material for phenoxy terminated TBBA, which is used PBT and polyester thermoplastic elastomer.
- Raw material for TBBA-diallylether used for polypropylene, surface waft and polystyrene foam
- Raw material for TBBA-bis(hydroxy ethyl ether) derivation used in production of unsaturated and saturated polyesters and Dacron-900 fiber.
- TBBA-bis(dibromopropyl ether) used for V-2-PP water pipes.

In these applications it is essential that TBBA used must be pure, free from reaction by-products, have very low ionic impurities good colour characteristics. In several manufacturing applications it is advantageous to use TBBA that is a free flowing powder or crystals with specified particle size distribution and angle of repose.

The prior art related to the preparation of TBBA has been focused at obtaining it in the most desired purity end characteristics for appropriate end applications.

The common method of preparation of TBBA is based on bromination of Bisphenol A according to the following reaction.

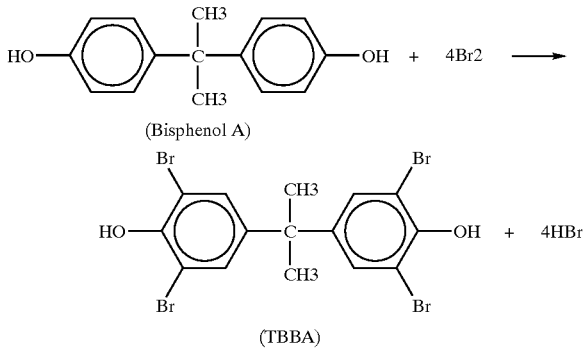

Small quantities of under brominated bisphenol components can also be formed in the reaction. It would be desirable to recover the HBr formed to utilise the bromine for bromination for cost optimisation and reduce contamination of the end product from the by-products and ionic impurities resulting from HBr. Several difficulties have been encountered in obtaining "high-purity" TBBA with "high-yields".

U.S. Pat. No. 3,548,302 (1970) uses two phase solvent systems consisting of 0.2–20 parts of water and one volume of unreactive "water-immiscible" liquid organic solvent such as CH2Cl2. The bromination is carried out under reflux conditions for 6 hours with gradual separation of TBBA The isolated TBBA has melting print 181–3 degree C. This process has severed problems related to recovery of HBr for re-use resulting in losses of expensive raw material.

German Patent no. 2227439 (1972) attempts to overcome the weaknesses in the re-use of HBr by introducing an aqueous solution of hydrogen peroxide in the reaction medium. Several other oxidising agents such as chorine, bromine for insitu convertion of HBr to Br2 in the reaction medium has been suggested. However, this suffered from problems of low yield (75–95%) of the crude product which included the di, tri and tetra brominated products. Repeated use of to mother liquor cold enhance the yields but make the process cumbersome and unsuitable for manufacture scale operations.

Japanese Patent no. 7955538 (1979) addresses the problem of separation of the brominated product from the emulsion obtained at the end of the reaction with the addition of above 100 ppm of a surface active agent. The yields continued to be in the range of 89.3% to 95.2% with unsatisfactory product quality. Another Japanese Patent 79119452 (1978) attempted the purification of TBBA by dissolving it in aqueous sodium hydroxide followed by addition of hydrochloric acid to reprecipitate the product. However, the end product suffered from colour problems, as the APHA (colour) of the end product did not go below 30.

Israeli Patent IL 64610 (1985) described a process of manufacture of TBBA in which the reaction of bisphenol A with bromine is carried out in the presence of a substantially "water-immiscible" organic solvent constituent and an aqueous constituent comprising hydrogen peroxide and by incorporating not more than 100 ppm of a surface active agent. The mother liquor resulting from the separation of the TBBA product is recycled to the reaction system. The final product was of 99.5% (by gas chromatography) and yield of 95%. This patent has however not commented on the colour characteristics (APHA) of the end product and the level of ionic impurities, which are critical in deciding on its end application.

U.S. Pat. No. 5,237,112 (1993) outlines a substantial improvement on earlier processes which involves bromination of bisphenol A in inert solvents, in the presence of hydrogen peroxide acidified with mineral acids (in quantities less than required to convert all, HBr formed to Br2). On completion of the reaction the reaction mass is boiled and the aqueous and non-aqueous phases are allowed to separate. The HBr co-product (with TBBA) in the non-aqueous phase is separate, washed with aqueous alkali sulphite solution and rinsed with deionised water. The final product is heat treated from 30 seconds to 1 hour. The end product is claimed to have <20 ppm ionic impurities. However this patent has claimed high yield "without disclosing" quantitative yield figures. The quality in terms of the colour (APHA) or texture of the end product has also not been disclosed. The emphasis of the U.S. patent is on reduction of ionic impurities by the extra heating process of the end product.

The Europe Patent Application No. EP372154 (1993) disclosed attempts to crystallize TBBA using alcohol to get large particle size single crystals ranging from 150–500 microns. However the process described are fraught with practical difficulties for industrial production.

Prior data EP 0672154 A1 also discloses single crystal tetrabromobisphenol A having an average particle size of 150 to 500 μm having a polyhedral shape of high quality having impurity reduced and having excellent powder properties and the process for its production. The TBBA obtained by the process have an angle of repose in the range 35° to 45°. Importantly, solvent used in such process is an alcohol solvent, which can lead to the production of undesired by-products. Also in such process, it is found to be extremely difficult and tedious to recover the solvent form the aqueous stream and involves complex recrystallation from an alcohol solvent. The process is further cost extensive as the same involves use of costly hydrazine hydrate for killing of bromine.

It is also known from prior dated U.S. Pat. No. 5,068,463 which corresponds to EP 0424895A of yet another process for the production of TBBA which suggest the washing of the organic phase containing dissolved tetrabromo-4,4-alkylidendephenol with an aqueous alkali sulphite solution preferably at 50–90° C. While this process outlines manufacture of TBBA of high purity, the product obtained is found to have APHA in the range of 10 to 70 HU. Also, the process involves the use of sulfuric add for bromination and washing is found to be not effective in removal of undesired iron content from the product.

Thus while several processes for manufacture of TBBA have been made available and known to the art over the years, it has not yet been possible to obtain the same having HPLC purity of 99.9% ionic bromide less than 10 ppm, angle of repose tae than 35° and alkaline APHA less than 100 HU. Also, particle size of such product of the known art are found to have limitation i.e. in the range of up to 250 μm only. Also the process for the manufacture of TBBA presently available in the art as discussed above we found to be complex and presently available in the art as discussed above are found to be complex and also cost-extensive. Thus for the above reasons, the industrial demand for processing with high yield and high purity TBBA still continues.

OBJECT OF THE INVENTION

It is thus the basic object of the present invention to provide TBBA of high purity having HPLC purity of 99.996 ionic bromides less than 10 ppm, angle of repose less than 35° and alkaline APHA less than 100 HU.

Another object is directed to a process of manufacture of TBBA of high purity as above with particle size ranging from 250 to 280 microns.

Another object of the present invention is to provide for a process for manufacture of TBBA of high purity which would enable obtaining TBBA of the above said purity and characteristics.

Another object of the present invention is directed to the process for manufacture of TBBA which would result in TBBA of high purity and characteristics as above and at the same time would be simple and cost effective.

A further object is directed to manufacture of TBBA using solvent which can be readily recovered and recycled to make the process cost effective.

Yet further object is directed to provide a process for manufacture of TBBA of high purity with yield of over 95%.

SUMMARY OF THE INVENTION

Thus the present invention relates to 4,4'-isopropylidene-bis-(2,6-dibromophenol) characterised by ionic bromides less than 10 ppm, colour in alkaline solution from 60–100 HU, HLPC purity about 99,99%, APHA of 20%

MeOH solution less than 10.0 HU; Fe less than 1.0 ppm, turbidity of 20% MeOH solution less than 5.0 NTU, pH of 10% slurry 6.0–7.0 average particle size of 250–280 microns and angle of repose equal to or less then 35°.

The present invention also relates to a process for preparation for high purity 4,4'-isopropylidine-bis-(2,6-dibromophenol) comprising a reaction of Bisphenol-A with bromine in a "water-immiscible" polar solvent in the presence of hydrogen peroxide, aging the reaction products after the reaction, eliminating the excess bromine by reducing agents, washing the product layer with a Combination of anionic surfactant, alkali, reducing agent and demineralised water under controlled pH conditions, partially distilling the organic solvent chilling the medium containing the product, filtering the crude product, boiling the crude product with alkali, reducing agent and demineralised water, filtering the TBBA, washing the product with demineralised water and drying to obtain the final high purity TBBA with high yield.

By the process there is obtained of free flowing TBBA in yields (~96.5%) and purities (99,9% by HPLC) mp 183° C. ionic bromides<10 ppm, colour or 20% alkaline solution<100 HU, with particle size 250–280 microns most suitable for the wide range of industrial applications.

DETAILED DESCRIPTION

The process in the present invention involves the following steps;

charging Bisphenol-A to water-immiscible "non-polor" and water;

feeding hydrogen peroxide in this mixture;

adding appropriate quantity of Bromine to the reaction mixture at a specified range of temperatures and time sufficient of tetrabrominate the Bisphenol A;

aging the reaction mixture;

destroying the excess bromine at the and of the reaction using Sodium Meta-bi-sulphite;

washing the product (non-aqueous phase) with a combination of anionic surfactant alkali, sodium meta-bi-sulphite and demineralised water;

distilling out major part of the solvent;

chilling the concentrated product layer and then filtering the crude product;

boiling the crude product with water, sodium meta-bi-sulphite and alkali ;

filtering the product and washing the cake with demineralised water;

drying the product.

The solvent used in the present invention may be selected from a wide range of non-polar solvents which have low solubility in water and these selected should demonstrate easy and speedy phase separation. Halogenated hydrocarbons halogenated aromatics and aromatics, chlorobenzene or ethylene dichloride are preferred. 5–10 moles of the solvent per mole of Bisphenol A is suitable. The strength of Hydrogen Peroxide may vary from 10–50% w/w.

Although in principle any surface-active agent can be used to ease the phase separation between the organic and aqueous layer, anionic surfactants are most suitable for enhanced phase separation and solvent recovery. 35–100 ppm of surfactant per mole of Bisphenol-A is adequate for the required purpose. The inventors have surprisingly found that washing the organic layer containing the product TBBA and co-product Br is best washed by a combination of demineralised water, alkali and sodium meta bi-sulphite at 75–90° C. maintaining pH from 2–4 during the washing stages. The alkali used may be alkali metal hydroxides, carbonates or their combinations. The washed organic layer containing TBBA may be chilled at 5–10° C. to obtain the crystals of TBBA. However, when 70–80% of the solvent in the organic layer is distilled and the concentrated organic layer is chilled the yield of crude TBBA is considerably increased. The entrapped or embedded ionic bromide in TBBA crystals varies from 30–40 PPM. Another significant finding of the present invention is the process of obtaining TBBA of very high purity. When the crude TBBA (continuing 30–40 PPM ionic bromide) is boiled with demineralised water, sodium meta bi-sulphite and alkali at a pH 5.5–6.0 and further washing of the recovered TBBA with demineralised water followed by normal drying at 70° C., a final product with ionic impurity <10 PPM is obtained. No heating at high temperatures or washing with surfactants etc. is necessary. The treatment in the present invention also ensures a product with high yield of good colour and textural characteristics.

The process of the invention is being illustrated by non-limiting examples.

EXAMPLE-1

Preparation of 4.4-iso Propylidine Bis-(2.6-dibromophenol)

Monochlorobenzene (480 ml) together 1 mole of Bisphenol-A, 100 ml water and 2.1 mole 30% w/w hydrogen peroxide were charged to 2 litre 3 necked flask with stirring arrangements, bromine addition facility and a thermowell. The reaction mass was vigorously stirred and 2.1 moles of bromine were added into the agitated solution. The heat of the reaction was removed by using ice-bath and maintained the temperature of the reaction mixture below 25° C. After the bromine addition the reaction mixture was maintained 45° C. for 2.0 hrs. and excess bromine was destroyed using 200 ml of 130-gpl sodium metabisulphite solution. To this reaction mass 0.035 gm of linear alkyl benzene sulphonic acid Was, added and stirred for 10 minutes and stopped stirring. The aqueous layer was separated and washed the organic layer using 500 ml water, 1 gram sodium metabisulphite and using 250 gpl soda ash solution to adjust the pH 2–4 to the aqueous washing. The washing was repeated three more times and distilled out 365.0 ml monochlorobenzene from the reaction mixture with the addition of 200 ml water and the reaction mass was chilled to 5° C., filtered the crude product and washed with 500 ml of DM water. Thus obtained crude product was having 32 PPM ionic bromides, which was boiled with 500 ml DM water; and 3.0 grams of sodium meta bi-sulphite and adjusted the pH 5.5–6.0 using 250 gpl soda ash solution. Finally the product was filtered, washed with 250 ml DM water and dried at 70° C.

Weight of the dry product=525 grams corresponding to a yield of 96.5%. The analysis of the product is—

| | | |
|---|---|---|
| 1. Melting point | : | 183° C. |
| 2. Purity (HPLC) | : | 99.9% |
| 3. Ionisable bromide | : | 08 ppm |
| 4. APHA of 20% MeOH solution | : | 6.0 |
| 5. pH of 10% sherry | : | 6.55 |
| 6. Colour of 20% alkaline solution | : | <100 HU |
| 7. Turbidity of 20% methanolic solution | : | 3.0 NTU |
| 8. Average particle size (90%) (Size of particles) | : | 275 microns (250–280 microns) |
| 9. Angle of repose | : | 35° |

EXAMPLE-2

The procedure followed was same as in example-1, but the monochlorobenzene distilled out was 350 ml instead of 365 ml.

Weight of the dry product = 525 grams
Corresponding to a yield of 96.5%
The analysis of the product indicated the following characteristics-

| | | |
|---|---|---|
| 1. Melting point | : | 183° C. |
| 2. Purity (HPLC) | : | 99.9% |
| 3. Ionisable bromide | : | <10 ppm |
| 4. APHA of 20% MeOH solution | : | 5.0 HU |
| 5. pH of 10% sherry | : | 6.12 |
| 6. Colour of 20% alkaline solution | : | <100 HU |
| 7. Turbidity of 20% methanolic solution | : | 2.4 NTU |
| 8. Average particle size (90%) (Size of particles) | : | 270 microns (250 to 280 microns) |
| 9. Angle of repose | : | 35° |

The essential feature of the product of this invention is its high purity (99.9% HPLC pure), methanolic APHA<10 HU, turbidity of 20% methanolic solution<5 NTU, pH of 10% slurry between 6.0–7.0, ionic bromides<10 PPM, colour of 20% alkaline solution<100 HU and average crystals sizes 250–280 microns with angle of repose 35° preferably less than 30°.

It is thus possible by way of the present invention to avoid the problems faced by the prior art and provide TBBA of high purity with particle size ranging from 260–280 microns angle of repose lesser than or equal to 30°, ionic bromide content less than 10 ppm Methanolic APHA values of less than 10.0 HU.

The process of the present invention makes use of water immiscible solvent so there are no harmful by products produced by side-reaction of the solvent. Also, the solvent is readily recovered and recycled so the present system has cost advantages.

The complex crystallization is avoided so the process is more streamlined. The process involves the use of Hydrogen peroxide and hence atomic proportion consumption of Bromine and also uses cheaper sodium metabisulphite for killing excess Bromine.

The process of the invention thus is both simple and cost effective to achieve high purity TBBA.

These characteristics make the product easily chargeable in industrial scale operations and result in end products without colour and contamination. The products obtained by the process of this invention can be effectively used for all the end use applications outlined herein.

What is claimed is:

1. 4,4'-isopropylidine-bis-(2,6-dibromophenol) characterized by ionic bromides less than 10 ppm, colour in alkaline solution from 60–100 HU, HPLC purity about 99.9%, APHA of 20% MeOH solution less than 10.0 HU, Fe less than 1.0 ppm, turbidity of 20% MeOH solution less than 5.0 NTU, pH of 10% slurry 6.0–7.0, average particle size of 250–280 microns and angle of repose equal to or less than 35°.

2. A process for preparation of high purity 4,4'-isopropylidine-bis-(2,6-dibromophenol) comprising a reaction of Bisphenol-A with bromine in a "water-immiscible" polar solvent in the presence of hydrogen peroxide, aging the reaction products after the reaction, eliminating the excess bromine by reducing agents, washing the product layer with a combination of anionic surfactant, alkali, reducing agent and demineralized water under controlled pH conditions, partially distilling the organic solvent chilling the medium containing the product, filtering the crude product, boiling the crude product with alkali, reducing agent and demineralized water, filtering the TBBA, washing the product with demineralized water and drying to obtain the final high purity TBBA with high yield.

3. A process according to claim 2, wherein the solvent is monochlorobenzene.

4. A process according to claim 2, wherein hydrogen peroxide used has strength of between 10–50% w/w.

5. A process according to claim 2, wherein the reducing agent is selected from sodium metabisulphite, sodium sulphite and sodium bisulphite.

6. A process according to claim 2, wherein the surfactant is selected from dioctyl sodium sulphosuccinate, naphthalene sulphonic acids, dodecyl benzene sulphonic acid, linear alkyl benzene sulphonic acid and the like in concentrations of 50–100 ppm per mole of Bisphenol-A.

7. A process according to claim 2, wherein the washing of the organic layer is carried out with an aqueous phase maintained at pH 2–4 and temperatures of between 75–90° C.

8. A process according to claim 2, wherein 65–80% of organic solvent is distilled.

9. A process according to claim 8, wherein the recovered solvent is reused.

10. A process according to claim 2, wherein the crystallization is effected in the concentrated organic layer by chilling it to 5–10 degrees centigrade.

11. A process according to claim 2, wherein the purification and crystallization of TBBA from the crude product is done in an integrated step by heating the crude TBBA in a solution comprising sodium metabisulphite in demineralized water whose pH is maintained at pH 5.5 to 6 with alkali metal hydroxides, carbonates or their combinations.

* * * * *